(12) United States Patent
Schena

(10) Patent No.: US 8,016,802 B1
(45) Date of Patent: Sep. 13, 2011

(54) METHOD, APPARATUS AND SYSTEM FOR OSTOMY BAG IRRIGATION

(76) Inventor: Kenneth R. Schena, Naples, FL (US)

(*) Notice: Subject to any disclaimer, the term of this patent is extended or adjusted under 35 U.S.C. 154(b) by 0 days.

(21) Appl. No.: 12/758,292

(22) Filed: Apr. 12, 2010

(51) Int. Cl.
*A61F 5/44* (2006.01)

(52) U.S. Cl. ........ 604/333; 604/332; 604/334; 604/335; 604/336; 604/337; 604/338; 604/339; 604/340; 604/341; 604/342; 604/343; 604/345; 137/8; 137/15.01; 137/15.04; 137/15.05; 239/696; 239/723; 239/726

(58) Field of Classification Search ........... 604/332, 604/333, 334, 335–345; 137/8, 15.01, 15.04, 137/15.05; 239/696, 723, 726; 127/8, 15.01, 127/15.04, 15.05

See application file for complete search history.

(56) References Cited

U.S. PATENT DOCUMENTS

| | | | | |
|---|---|---|---|---|
| 935,071 A * | 9/1909 | Vossler | ............................ | 239/261 |
| 3,752,472 A * | 8/1973 | Snead | ............................ | 482/35 |
| 4,084,590 A * | 4/1978 | Caraway et al. | ............................ | 604/335 |
| 4,192,255 A * | 3/1980 | Willinger | ............................ | 119/263 |
| 4,468,227 A * | 8/1984 | Jensen | ............................ | 604/327 |
| 4,654,037 A * | 3/1987 | Fenton | ............................ | 604/334 |
| 4,911,699 A * | 3/1990 | Fenton | ............................ | 604/333 |
| 4,941,869 A * | 7/1990 | D'Amico | ............................ | 600/32 |
| 5,470,325 A * | 11/1995 | Fundock | ............................ | 604/332 |
| 6,224,581 B1 * | 5/2001 | Withers et al. | ............................ | 604/334 |
| 6,408,861 B1 * | 6/2002 | Ortega | ............................ | 134/100.1 |
| 7,090,664 B2 * | 8/2006 | Holter | ............................ | 604/332 |
| 7,722,583 B2 * | 5/2010 | Kim et al. | ............................ | 604/317 |
| 7,815,618 B2 * | 10/2010 | Schena et al. | ............................ | 604/337 |
| 7,842,018 B2 * | 11/2010 | Schena et al. | ............................ | 604/344 |
| 2006/0111682 A1 * | 5/2006 | Schena et al. | ............................ | 604/334 |

* cited by examiner

*Primary Examiner* — Melanie J Hand
*Assistant Examiner* — Ginger T Chapman
(74) *Attorney, Agent, or Firm* — Maier & Maier, PLLC

(57) ABSTRACT

A manifold for ostomy bag irrigation, including an inlet member having a channel defined therein, a T-member having a channel defined therein and in fluid communication with the inlet member, a left tube having a plurality of apertures defined therein and having one end coupled to the T-member, a right tube having a plurality of apertures defined therein and having one end coupled to the T-member, a left cap having a channel defined therein and coupled to the second end of the left tube, and a right cap having a channel defined therein and coupled to the second end of the right tube.

20 Claims, 2 Drawing Sheets

METHOD, APPARATUS AND SYSTEM FOR OSTOMY BAG IRRIGATION

BACKGROUND

An ostomy is a surgical procedure in which an organ, for example the colon or a portion thereof, is removed and the digestive tract is attached to an opening surgically created in the abdominal wall, thereby, allowing digested waste to pass through the abdomen. Examples of ostomies include colostomies, ileostomies and urostomies, amongst others. Typically, the waste is then collected by an impervious bag that is secured over the opening. The opening that results from a colonectomy, or other similar procedures is known as an a "stoma," and the impervious bag that collects the digestive waste is generally known as an ostomy bag.

An individual who has had a colostomy, ileostomy or the like typically empties the ostomy bag one or more times a day. Additionally, there are varying procedures for irrigating the stoma, which may be done on an about daily basis to maintain good health and sanitation. An ostomy is typically irrigated by applying warm flowing water into the ostomy, maintaining it for a predetermined amount of time and then allowing the water and any waste to drain there from.

SUMMARY

In one exemplary embodiment, a manifold for ostomy bag irrigation is disclosed. The manifold may include an inlet member having a channel defined therein, a T-member having a channel defined therein and in fluid communication with the inlet member, a left tube having a plurality of apertures defined therein and having one end coupled to the T-member, a right tube having a plurality of apertures defined therein and having one end coupled to the T-member, a left cap having a channel defined therein and coupled to the second end of the left tube, and a right cap having a channel defined therein and coupled to the second end of the right tube.

In another exemplary embodiment, a method of utilizing a manifold for ostomy bag irrigation in conjunction with an ostomy bag is disclosed. The method may include defining a passage between the inner cavity of an ostomy bag and the exterior of the ostomy bag, coupling a right tube and a left tube to a T-member, inserting the right tube, left tube and T-member into the inner cavity of an ostomy bag, coupling the T-member to an inlet member disposed on the exterior of the bag via said passage, and adhering the inlet member and T-member to the ostomy bag such that a liquid-tight seal is formed.

In another exemplary embodiment, a method of irrigating an ostomy bag is disclosed. The method may include applying positive liquid pressure to the inlet member of a manifold for ostomy bag irrigation that is coupled to an ostomy bag, splitting the positive liquid pressure between a right tube and a left tube, the right tube and the left tube each having a plurality of apertures defined therein, and directing the positive liquid pressure through the plurality of apertures into an inner cavity of the ostomy bag.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1A:
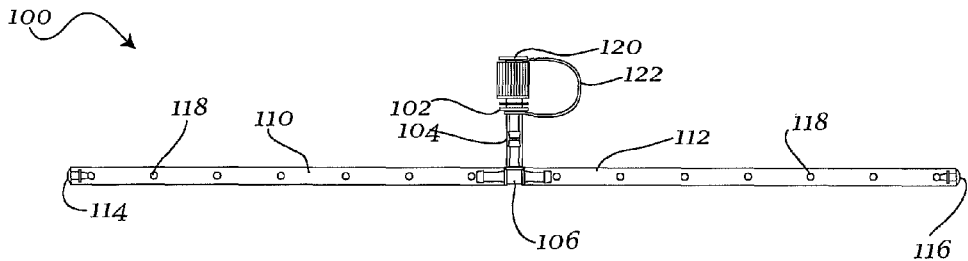
FIG. 1a shows an exemplary embodiment of a manifold for ostomy bag irrigation in an assembled configuration.
Figure 1B:
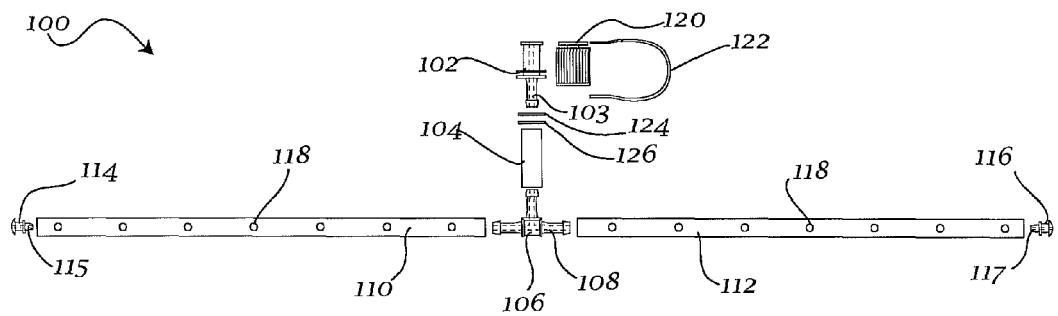
FIG. 1b shows an exemplary embodiment of a manifold for ostomy bag irrigation in a disassembled configuration.
Figure 1C:
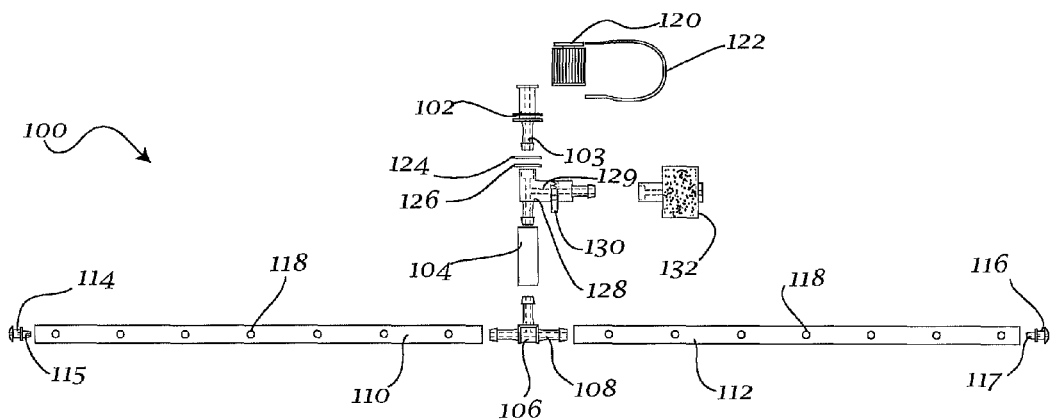
FIG. 1c shows another exemplary embodiment of a manifold for ostomy bag irrigation in a disassembled configuration.

Turning to FIGS. 1a-1c, a manifold 100 for irrigation of an ostomy bag is shown. Manifold 100 may include an inlet member 102, a first tube 104, a T-member 106, left and right irrigation tubes 110, 112, and left and right plugs 114, 116. Manifold 100 may further include a cap 120 and lanyard 122, the cap 120 being sized and threaded to threadably couple with inlet member 102 such that a liquid proof or liquid-tight seal can be formed. Manifold 100 may further include a first adhesive ring 124 and a second adhesive ring 126. Adhesive rings 124, 126 may facilitate coupling manifold 100 to an ostomy bag. In another embodiment, adhesive strips, gels, liquids, or any other adhesives known in the art that enable manifold 100 to function as described herein may be used in lieu of adhesive rings 124, 126. In still further examples, a valve (not shown) may be associated with manifold 100 and may allow for metering or control of any liquid flowing therethrough.

First tube 104, and left and right irrigation tubes 110, 112 may be formed from any flexible, resilient material known in the art. First tube 104 may also be sized to sealably couple with inlet member 102 and T-member 106, while left irrigation tube 110 may be sized to sealably couple with T-member 106 and left plug 114, and right irrigation tube may be sized to sealably couple with T-member 106 and right plug 116. Coupling between the above-described components may be facilitated by pressure fitting tubes 104, 110, 112 over the ends of inlet member 102, T-member 106 and left and right caps 114, 116. In one embodiment, the deformation of tubes 104, 110, 112 upon coupling with the ends of members 102, 106 and caps 114, 116 may be sufficient to maintain the coupling of the components of manifold 100 to each other when liquid pressure is applied to manifold 100 such that a liquid-tight seal exists. In another embodiment, an adhesive may be applied to the components of manifold 100 such that coupling is maintained under liquid pressure.

Left irrigation tube 110 and right irrigation tube 112 may each include a plurality of apertures 118. In one embodiment, apertures 118 may be positioned in diametrically opposed pairs, that is, for every aperture 118 disposed along the axial length of tube 110 or tube 112, there may be a corresponding aperture 118 disposed at the same axial position along the length of tube 110 or tube 112, but facing an opposite side of tube 110 or tube 112 in relation to the paired aperture. Such a structure can facilitate directing the liquid flow in equal and opposite directions from tubes 110, 112. In one exemplary embodiment, each of tubes 110, 112 may have seven pairs of diametrically opposed apertures 118 disposed along its axial length. In other exemplary embodiments, any number of apertures 118 may be arranged or disposed in any desired manner.

Inlet member 102 may have a channel 103 defined therein. Channel 103 may facilitate the flow of liquid through inlet member 102 into first tube 104. Channel 103 may be sized such that a desired rate of liquid flow and a desired liquid pressure are achieved during use of manifold 100. T-member 106 may have a channel 108 defined therein. Channel 108 may facilitate the flow of liquid from first tube 104 through T-member 106 and into left and right tubes 110, 112. Channel 108 may be bifurcated such that direction of liquid flow is facilitated in equal and opposite directions into tubes 110, 112. Left and right caps 114, 116 may also have channels 115, 117 defined therein. Channels 115, 117 may facilitate the flow of liquid from left and right tubes 110, 112, through left and right caps 114, 116 and out of manifold 100. Therefore, a liquid flowing from a liquid source coupled to inlet member 102 is distributed via manifold 100 and its constituent components into a plurality of liquid streams or sprays that may emanate from apertures 118, channel 115 of left cap 114, and channel 117 of right cap 116. The result, therefore, can be a plurality of liquid streams or sprays that facilitate evenly cleaning an ostomy bag that is being used in conjunction with manifold 100.

In another exemplary embodiment, as shown in FIG. 1c, manifold 100 may further include a valve 128 and charcoal filter 132. Valve 128 may include a channel 129 defined therein and may be configured to sealably couple with first tube 104, inlet member 102 or T-member 106, and charcoal filter 132. Valve 128 may further include button 130, which may be disposed in a closed position within valve 128 such that fluid communication between channel 129 and charcoal filter 132 can be blocked. When an ostomy bag is in use, gases may build up within the ostomy bag, which may cause turgidity of the ostomy bag and discomfort for the patient. In such a case, the user may depress button 130, facilitating fluid communication between channel 129 and charcoal filter 132. In other exemplary embodiments, valve 128 may be actuated by a trigger, a squeeze valve, or any other selectively openable valve known in the art. Consequently, gases may escape from the ostomy bag via charcoal filter 132, thereby reducing the interior pressure of the ostomy bag. Furthermore, charcoal filter 132 can facilitate the minimization of unpleasant odors that may emanate from the ostomy bag. Also, in some further exemplary embodiments, charcoal filter 132, and any component associated therewith, may be mounted in any desired fashion or otherwise coupled to manifold 100 in any desired manner. For example, in some exemplary embodiments, charcoal filter 132, or any other desired type of filter, may be connected to or coupled with any portion of manifold 100.

Figure 2A:
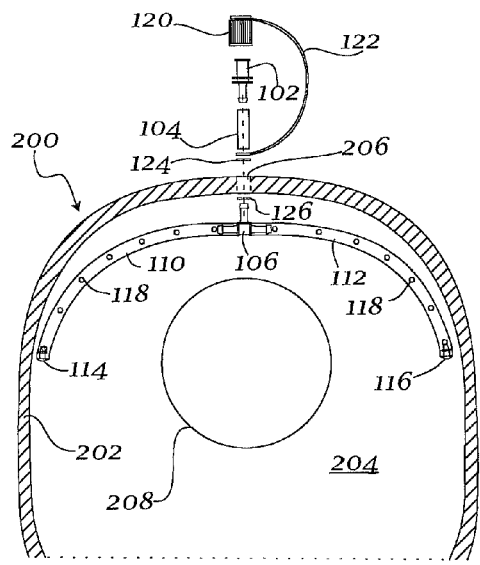
FIG. 2a shows an exemplary coupling of a manifold for ostomy bag irrigation to an ostomy bag.
Figure 2B:
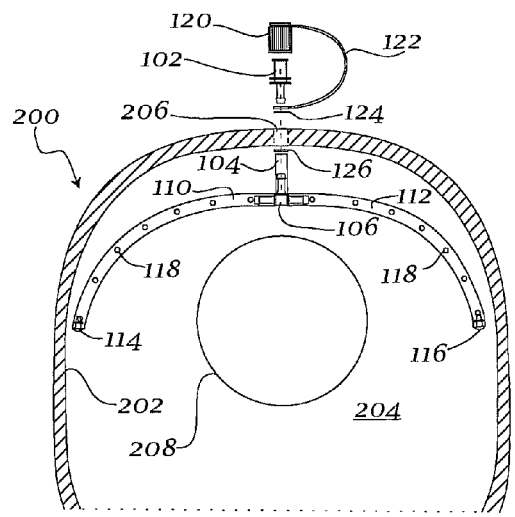
FIG. 2b shows another exemplary coupling of a manifold for ostomy bag irrigation to an ostomy bag.

FIGS. 2a-2b show exemplary installations of manifold 100 in an ostomy bag 200. Generally, ostomy bags are formed from a plurality of layers 202 that are sealed, by heat-sealing or any other methods known in the art, to form a liquid-tight border that defines an inner cavity 204. Additionally, ostomy bags generally include an inlet opening 208 and an outlet opening 209 (shown in FIGS. 3a-3b). In some examples, inlet opening 208 couples to a stoma and further can be predefined in known variations of ostomy bags.

Referring to FIG. 2a, in one exemplary embodiment of installing manifold 100 in an ostomy bag 200, layers 202 of ostomy bag 200 may be punctured by a narrow, sharp object, such as a pin, knife, awl, scissors or any other such object known in the art. Puncturing layers 202 defines a passage 206 between inner cavity 204 and the exterior of ostomy bag 200. Layers 202 may be punctured at a region substantially near the center and top of ostomy bag 200 in order to facilitate a desired fitting of manifold 100 within ostomy bag 200. At this point, T-member 106, right and left tubes 110, 112 and right and left caps 114, 116 may be coupled together as described earlier herein. Bottom adhesive ring 126 may then be placed over the vertical portion of T-member 106. The assembled components may then be inserted into cavity 204 of ostomy bag 200 via inlet opening 208. Right and left tubes 110, 112 may be resiliently deformed as desired such that they substantially conform with the inner contours of the ostomy bag. The vertical portion of T-member 106 may then be inserted through passage 206 and pressed together with layers 202 of ostomy bag 200 such that a liquid-tight seal is formed between layers 202, bottom adhesive ring 126, and T-member 106. The liquid-tight seal can prevent the passing of the contents of ostomy bag 200 through passage 206. Subsequently, inlet member 102, first tube 104, as well as cap 120 and lanyard 122 may then be coupled together. Top adhesive ring 124 may then be placed between the bottommost of the above-mentioned components (this may be first tube 104 or lanyard 122) and the outer layer of ostomy bag 202. First tube 104 may then be press-fitted onto the vertical portion of T-member 106, thereby coupling all components of manifold 100 and forming a liquid-tight seal between first tube 104 or lanyard 122, top adhesive ring 124, and the outer layer of ostomy bag 200. The liquid-tight seal can prevent the passing of the contents of ostomy bag 200 through passage 206. In some exemplary embodiments, valve 128 and filter 132 may also be coupled to manifold 100 such that valve 128 and filter 132 are disposed between inlet member 102 and T-member 106.

Referring to FIG. 2b, in another exemplary embodiment of installing manifold 100 in an ostomy bag 200, layers 202 of ostomy bag 200 may be punctured by a narrow, sharp object, such as a pin, knife, awl, scissors or any other such object known in the art. Puncturing layers 202 defines a passage 206 between inner cavity 204 and the exterior of ostomy bag 200. Layers 202 may be punctured at a region substantially near the center and top of ostomy bag 200 in order to facilitate a desired fitting of manifold 100 within ostomy bag 200. At this point, inlet member 102 and cap 120 and lanyard 122 may then be coupled together. Top adhesive ring 124 may then be placed between lanyard 122 and the outer layer of ostomy bag 202. The bottom portion of inlet member 102 may then be inserted through passage 206 and pressed together with the surface layer of ostomy bag 200 such that a liquid-tight seal may be formed between inlet 104, lanyard 122, top adhesive ring 124 and the surface layer of ostomy bag 200. The liquid-tight seal can prevent the passing of the contents of ostomy bag 200 through passage 206. Subsequently, first tube 104, T-member 106, right and left tubes 110, 112 and right and left caps 114, 116 may be coupled together as described earlier herein. Bottom adhesive ring 126 may then be placed between the top end of first tube 104. The assembled components may then be inserted into cavity 204 of ostomy bag 200 via inlet opening 208. Right and left tubes 110, 112 may be resiliently deformed as desired such that they substantially conform with the inner contours of the ostomy bag. First tube 104 may then be press-fitted onto the bottom portion of inlet member 106, thereby coupling all components of manifold 100 and forming a liquid-tight seal between first tube 104, bottom adhesive ring 124, and the inner layer 202 of ostomy bag 200. The liquid-tight seal can prevent the passing of the contents of ostomy bag 200 through passage 206. In some exemplary embodiments, valve 128 and filter 132 may also be coupled to manifold 100 such that valve 128 and filter 132 are disposed between inlet member 102 and T-member 106.

Figure 3A:
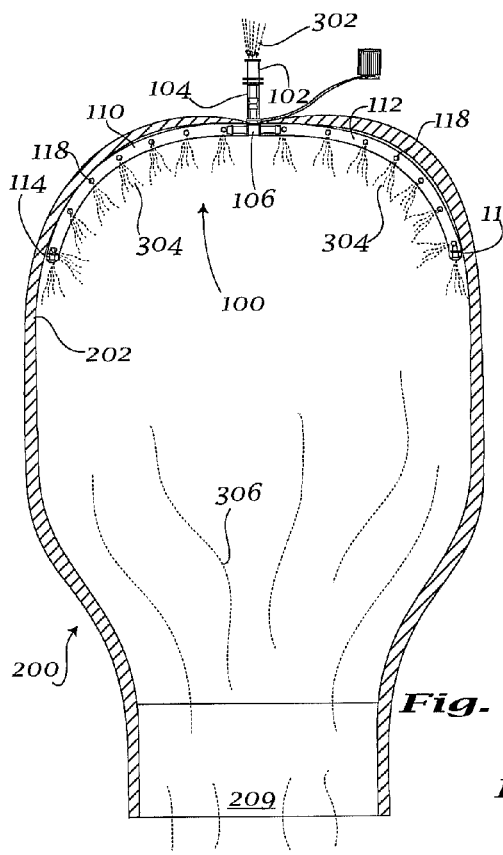
FIG. 3a illustrates an exemplary irrigation of an ostomy bag.
Figure 3B:
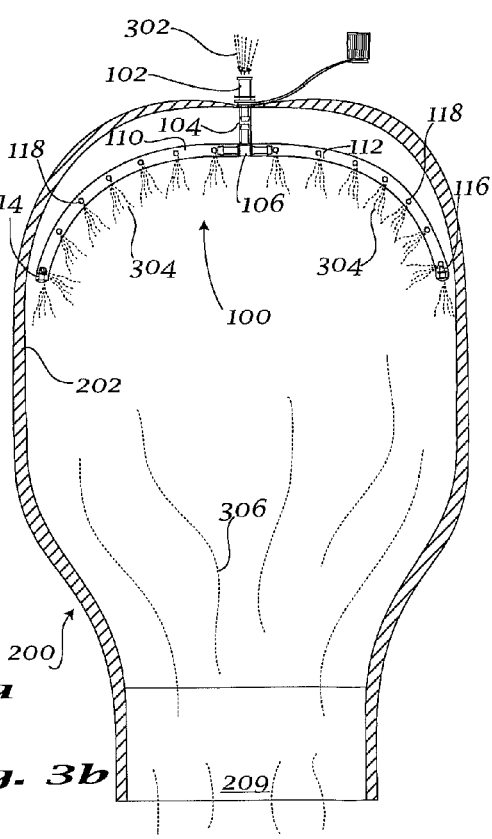
FIG. 3b illustrates another exemplary irrigation of an ostomy bag.

Turning to FIGS. 3a-3b, an exemplary method of utilizing manifold 100 to irrigate an ostomy bag 200 is shown. It should be noted that FIG. 3a illustrates a manifold 100 coupled to an ostomy bag 200 by the exemplary method of FIG. 2a, while FIG. 3b illustrates a manifold 100 coupled to an ostomy bag 200 by the exemplary method of FIG. 2b. However, the method of irrigation is substantially the same in both cases.

In an exemplary method of utilizing manifold 100 to irrigate an ostomy bag 200, positive liquid pressure 302 may be applied to inlet member 102 of manifold 100. The positive liquid pressure 302 may be applied from any liquid source, for example, but not limited to via a conduit that may be capable of coupling to inlet member 102 of manifold 100, such as a flexible hose having an end fitting that can threadably couple to inlet member 102. Under pressure, the liquid can be forced through inlet portion 102, tube 104 and may then be split via T-member 106 and directed towards left and right tubes 110, 112. The liquid can then be forced through the plurality of diametrically opposed apertures 118 (or any other desired arrangement of apertures 118), that are defined in tubes 110, 112 as well as through channels 115, 117 that are defined within left and right caps 114, 116. The resultant pressurized streams or sprays of liquid 304 that emanate from apertures 118 and channels 115, 117 may evenly and thoroughly clean any contents of interior cavity 204 of ostomy bag 200. The effluent 306 is then discharged from ostomy bag 200 via the bottom opening 209 of ostomy bag 200. Irrigation of ostomy bags with convenience, minimal effort and cleanliness may thus be achieved.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:
1. A manifold for ostomy bag irrigation, comprising:
an inlet member having a channel defined therein;
a T-member having a channel defined therein and in fluid communication with the inlet member;
a left tube having a plurality of apertures defined therein and having a first end coupled to the T-member;
a right tube having a plurality of apertures defined therein and having a first end coupled to the T-member;
a left cap having a channel defined therein and coupled to a second end of the left tube; and
a right cap having a channel defined therein and coupled to a second end of the right tube, wherein each of the inlet member, the T-member, the left tube, the right tube, the left cap and the right cap are separable.

2. The manifold of claim 1, wherein the right tube and left tube are resiliently deformable.

3. The manifold of claim 2, further comprising:
a first tube coupled to the inlet member and the T-member;
a cap removably coupled to the inlet member; and
a lanyard coupled to the cap and coupled to the inlet member or the T-member.

4. The manifold of claim 3, further comprising:
an upper adhesive disposed between the inlet member and the T-member.

5. The manifold of claim 4, further comprising:
a lower adhesive disposed between the upper adhesive and the T-member.

6. The manifold of claim 2, further comprising:
a selectively openable outlet coupled to a filter.

7. The manifold of claim 6, wherein the selectively openable outlet comprises a valve.

8. The manifold of claim 6, wherein the selectively openable outlet is actuated by a button.

9. The manifold of claim 6, wherein the filter comprises a charcoal filter.

10. A method of utilizing a manifold for ostomy bag irrigation in conjunction with an ostomy bag, comprising:
defining a passage between the inner cavity of an ostomy bag and the exterior of the ostomy bag;
separably coupling a right tube and a left tube to a T-member;
separably coupling the right tube to a right cap having a channel defined therein;
separably coupling the left tube to a left cap having a channel defined therein;
removably inserting the right tube, left tube and T-member into the inner cavity of an ostomy bag;
separably coupling the T-member to an inlet member disposed on the exterior of the bag via said passage; and
adhering the inlet member and T-member to the ostomy bag such that a liquid-tight seal is formed.

11. The method of claim 10, further comprising:
resiliently deforming the right tube and left tube such that the right tube and left tube substantially conform to the inner contour of the ostomy bag.

12. The method of claim 10, further comprising:
inserting the right tube, left tube and T-member into the inner cavity via the inlet opening.

13. The method of claim 10, further comprising:
inserting the right tube, left tube and T-member into the inner cavity via the outlet opening.

14. The method of claim 10, wherein defining a passage between the inner cavity of an ostomy bag and the exterior of the ostomy bag further comprises defining said passage substantially near the top end of the ostomy bag.

15. The method of claim 10, further comprising:
coupling a selectively openable outlet to the inlet member and the T-member; and
coupling a filter to the outlet.

16. The method of claim 15, wherein the selectively openable outlet is a valve.

17. The method of claim 15 wherein the selectively openable outlet is actuated by a button.

18. The method of claim 15, wherein the filter comprises a charcoal filter.

19. A method of irrigating an ostomy bag, comprising:

applying positive liquid pressure to an inlet member of a manifold for ostomy bag irrigation that is coupled to an ostomy bag;

separably coupling the inlet member, a T-member, a left tube and a right tube;

separably coupling the right tube to a right cap having a channel defined therein;

separably coupling the left tube to a left cap having a channel defined therein;

splitting the positive liquid pressure through the T-member between the right tube and the left tube, the right tube and the left tube each having a plurality of apertures defined therein; and directing the positive liquid pressure through the plurality of apertures into an inner cavity of the ostomy bag.

20. The method of claim 19, further comprising:

separably coupling a liquid source to the inlet member of a manifold for ostomy bag irrigation that is coupled to an ostomy bag.

* * * * *